(12) United States Patent
Brush

(10) Patent No.: US 10,650,478 B2
(45) Date of Patent: May 12, 2020

(54) REAL-TIME AGGREGATION AND PROCESSING OF HEALTHCARE RECORDS

(75) Inventor: Ryan Alan Brush, Overland Park, KS (US)

(73) Assignee: CERNER INNOVATION, INC., Overland Park, KS (US)

(*) Notice: Subject to any disclaimer, the term of this patent is extended or adjusted under 35 U.S.C. 154(b) by 961 days.

(21) Appl. No.: 13/457,758

(22) Filed: Apr. 27, 2012

(65) Prior Publication Data

US 2013/0290020 A1  Oct. 31, 2013

(51) Int. Cl.
*G16H 10/60* (2018.01)
*G06Q 50/24* (2012.01)

(52) U.S. Cl.
CPC .......... *G06Q 50/24* (2013.01); *G16H 10/60* (2018.01)

(58) Field of Classification Search
CPC .................. G06C 50/22–24; G16H 10/60
See application file for complete search history.

(56) References Cited

U.S. PATENT DOCUMENTS

| | | | | |
|---|---|---|---|---|
| 2002/0007284 A1* | 1/2002 | Schurenberg | .......... | G06Q 10/10 705/2 |
| 2005/0114179 A1* | 5/2005 | Brackett et al. | .................. | 705/2 |
| 2006/0184489 A1* | 8/2006 | Weiner | .................. | G16B 50/00 706/46 |
| 2007/0055552 A1* | 3/2007 | St Clair | .............. | G06F 19/3481 705/3 |
| 2008/0104104 A1* | 5/2008 | Nolan | .................. | G06Q 10/06 |
| 2008/0133273 A1* | 6/2008 | Marshall | ............................ | 705/3 |
| 2008/0306764 A1* | 12/2008 | Weiss-Meilik | .................... | 705/2 |
| 2009/0171695 A1* | 7/2009 | Cobbinah | .............. | G06Q 50/24 705/3 |
| 2009/0172773 A1* | 7/2009 | Moore | .................. | G06F 19/325 726/1 |
| 2009/0192823 A1* | 7/2009 | Hawkins | .............. | G06F 19/321 705/3 |
| 2009/0216562 A1* | 8/2009 | Faulkner et al. | ................. | 705/3 |
| 2009/0228303 A1* | 9/2009 | Faulkner et al. | ................. | 705/3 |
| 2009/0254376 A1* | 10/2009 | Martinez et al. | ................. | 705/3 |
| 2010/0131293 A1* | 5/2010 | Linthicum | ............. | G06Q 50/24 705/3 |
| 2011/0087652 A1* | 4/2011 | Westin | .................. | G06F 19/321 707/722 |
| 2011/0178821 A1* | 7/2011 | Smith | ............................. | 705/3 |
| 2011/0257998 A1* | 10/2011 | Cinqualbre et al. | ............. | 705/3 |
| 2012/0065987 A1* | 3/2012 | Farooq | .................. | G06F 19/328 705/2 |
| 2012/0065995 A1* | 3/2012 | Singh | .................... | G06Q 50/24 705/3 |

(Continued)

*Primary Examiner* — Robert A Sorey
(74) *Attorney, Agent, or Firm* — Shook, Hardy & Bacon LLP

(57) ABSTRACT

Methods, computer systems, and computer storage media are provided for utilizing clinical information in disparate formats or structures to generate multiple derived representations of the clinical information, each derived representation structured to meet a particular clinical need. Clinical information is aggregated from multiple, disparate data sources; the clinical information is in a first format. The information is restructured to generate a derived representation of the information; the derived representation is in a second format. The derived representation is communicated to a clinical application that meets the particular clinical need.

11 Claims, 7 Drawing Sheets

(56) References Cited

U.S. PATENT DOCUMENTS

| | | | |
|---|---|---|---|
| 2012/0130730 A1* | 5/2012 | Setlur et al. | 705/2 |
| 2012/0179490 A1* | 7/2012 | Fuhrmann et al. | 705/3 |
| 2012/0278105 A1* | 11/2012 | Luszcz | G06F 19/321 |
| | | | 705/3 |
| 2012/0323601 A1* | 12/2012 | Huang | G16H 10/60 |
| | | | 705/3 |
| 2013/0034279 A1* | 2/2013 | Cosatto et al. | 382/128 |
| 2013/0034304 A1* | 2/2013 | Cosatto et al. | G06K 9/00979 |
| | | | 382/190 |
| 2013/0041971 A1* | 2/2013 | Bhogal et al. | 709/213 |
| 2013/0191157 A1* | 7/2013 | Eiden et al. | 705/3 |

* cited by examiner

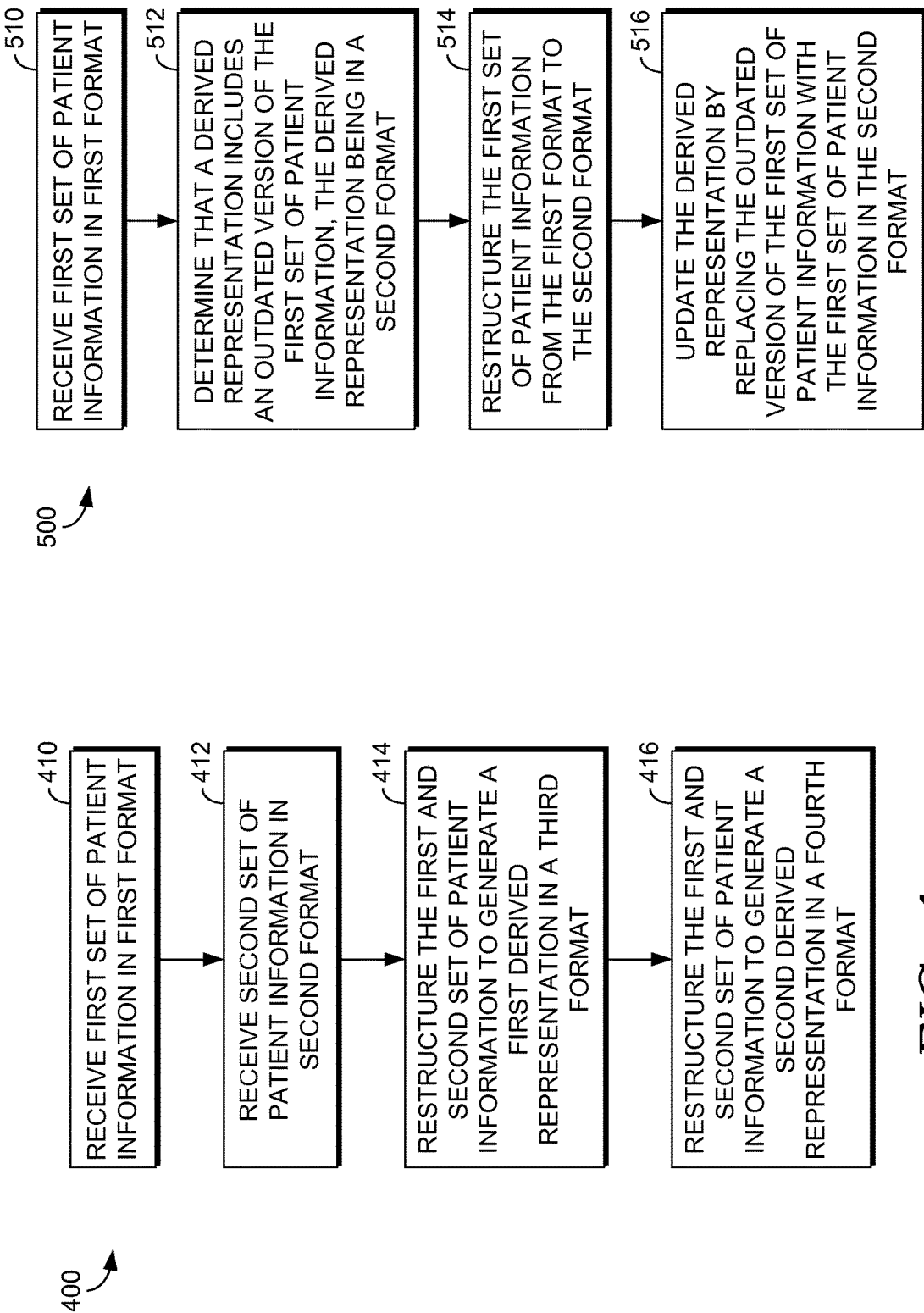

800

| WIRELESS 📶 | 10:49 AM | 100% 🔋 |

MINCHUM, IMMA

HINES, ANNA MARIA  37Y F  DOB: 08/16/1974
REASON FOR VISIT: RASH  (12/13/2011) BLUE CLINIC ROOM 4

ORDERS  [+] [⋯] [📍] [SIGN]

MEDICATIONS ～ 810

| AUGMENTIN 400 MG/5 ML ORAL | REFILL | COMPLETE | DISCONTINUE |
| =5 ML, PO, Q12HR | | | |

| CERZIL 250 MG/5 ML ORAL | REFILL | COMPLETE | DISCONTINUE |
| 250 MG, PO, TID, 20 TABS | | | |

| IBUPROFEN 800 MG ORAL TABLET | REFILL | COMPLETE | DISCONTINUE |
| 800 MG, PO, TID, 20 TABS | | | |

| GLUCOPHAGE 500 MG ORAL TABLET | REFILL | COMPLETE | DISCONTINUE |
| 500 MG, PO, BID, 60 TABS, 2 REFILLS | | | |

| METFORMIN 500 MG ORAL TABLET | REFILL | COMPLETE | DISCONTINUE |
| 500 MG, PO, BID, 60 TABS, 30 DAYS | | | |

LABS ～ 812

| CBC | INITIATE | DISCONTINUE |
| BLOOD, ROUTINE LAB COLLECTION, COUGH, FOR 1 DAY, 1/11/2011 8:05 | | |

| BASIC METABOLIC PANEL | INITIATE | DISCONTINUE |
| BLOOD, ROUTINE LAB COLLECTION, DIABETES MELLITUS, TYPE 2, FOR 1 DAY, 1/11/2011 8:05 | | |

IMAGING ～ 814

| XR CHEST 2 VIEWS (CXR) | INITIATE | DISCONTINUE |
| ROUTINE, COUGH, TRANSPORT MODE AMPULATE | | |

*FIG. 8.*

REAL-TIME AGGREGATION AND PROCESSING OF HEALTHCARE RECORDS

BACKGROUND

A patient's healthcare information tends to be fragmented across multiple, disparate electronic medical record systems (EMR systems). Oftentimes this is because patients visit multiple medical facilities, each having its own EMR system, to meet their different healthcare needs. For instance, a patient may have an EMR with his or her primary care physician, but this EMR may not be shared with any other medical facilities that are involved in treating the patient, such as an emergency room, a specialist, etc. Instead, the patient would have an EMR with each of the other medical facilities. The information in each of the EMRs may be structured differently depending on the characteristics of the EMR system. The result is that patient information is not typically shared between different facilities, which may impair clinicians in their treatment of patients, as clinicians are unable to see the full scope of the patient's condition.

Even within the confines of a single EMR at a single facility, the information may be split between different data models or tables. Combinations of data from these different models are often needed to create a complete view of a patient's state and prognosis. This view is typically created by repeatedly querying the separate data models in an attempt to generate a cohesive view of the information. This can consume significant resources of the underlying system and introduces latency between when the data was modified and the corresponding view updated.

Further, the way EMR systems structure the underlying medical records may not be optimal for all clinical applications. Some EMRs are structured using a relational model, while other EMRs are structured in a hierarchical model. No single model is ideal for all possible query patterns. For example, a lab result may be queried as part of a flowsheet showing the current status of a patient, as part of a broader timeline showing the history of the patient, grouped with similar tests to show a recent trend, or searchable by some arbitrary criteria. The structure of the data in the EMR will not be optimal for all these different query patterns, meaning that some clinical applications may be prohibitively expensive to generate.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief, and at a high level, the present invention is directed to methods, systems, and computer-readable storage media for utilizing clinical information in disparate formats or structures to generate multiple derived representations of the clinical information, each derived representation structured to meet a particular clinical need. Clinical information is received from one or more medical organizations; the clinical information may be structured in any number of different formats. The clinical information is reformatted in different ways to create a variety of derived representations of the information. In turn, these derived representations are immediately available for use by clinical applications. The derived representations are updated in real time whenever clinical information is modified or updated at the medical organizations. Further, new derived representations may be quickly created as new clinical needs evolve.

BRIEF DESCRIPTION OF THE DRAWINGS

Embodiments are described in detail below with reference to the attached drawing figures, wherein:

FIG. 4 is a flow diagram of an exemplary method of utilizing clinical information in disparate formats to generate one or more derived representations of the clinical information in accordance with an embodiment of the present invention;

FIG. 5 is a flow diagram of an exemplary method of updating derived representation of patient information in accordance with an embodiment of the present invention;

FIG. 8 depicts an exemplary graphical user interface for presenting on a single user interface clinical information from disparate electronic medical record systems in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

In brief, and at a high level, the present invention is directed to methods, systems, and computer-readable storage media for utilizing clinical information in disparate formats or structures to generate multiple derived representations of the clinical information, each derived representation structured to meet a particular clinical need. Clinical information is received from one or more medical organizations; the clinical information may be structured in any number of different formats. The clinical information is reformatted in different ways to create a variety of derived representations of the information. In turn, these derived representations are immediately available for use by clinical applications. The derived representations are updated in real time whenever clinical information is modified or updated at the medical organizations. Further, new derived representations may be quickly created as new clinical needs evolve.

Figure 1:
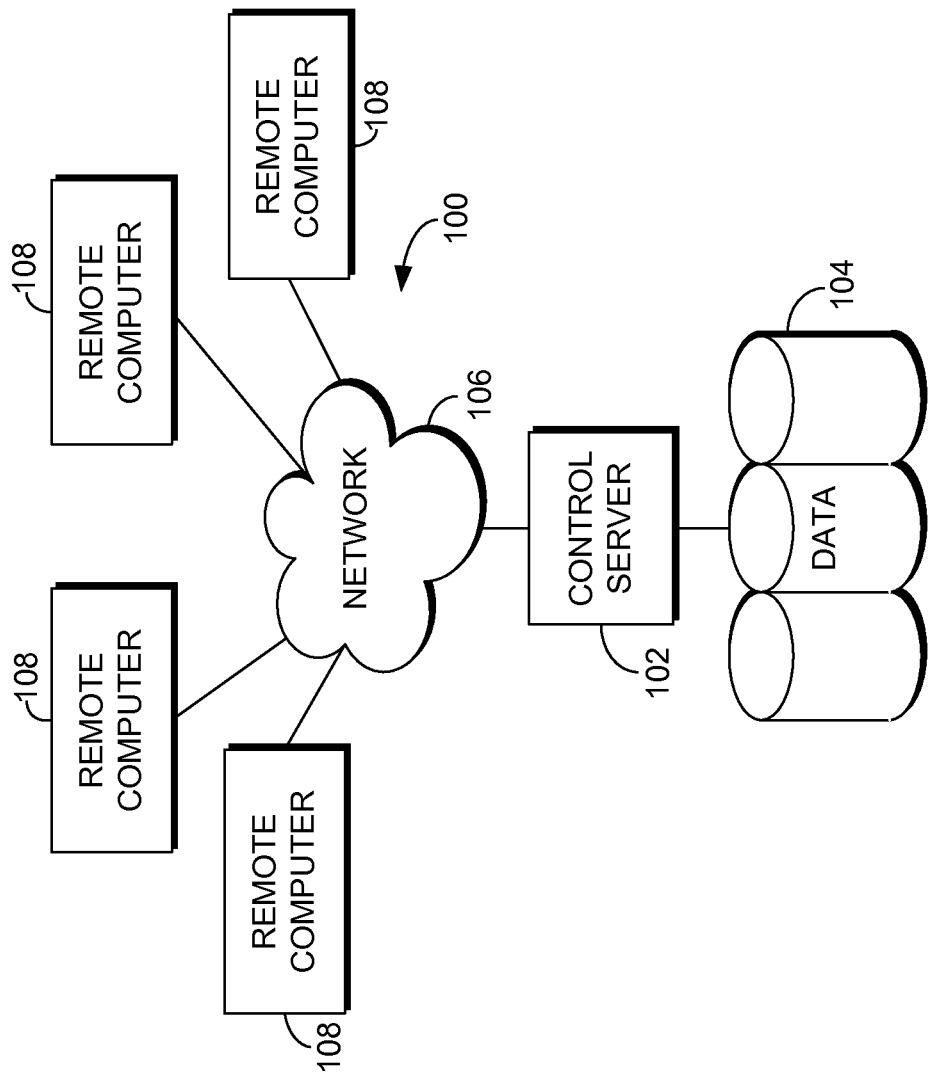
FIG. 1 is a block diagram of an exemplary computing environment suitable to implement embodiments of the present invention.

Having provided a high-level overview of the present invention, an exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
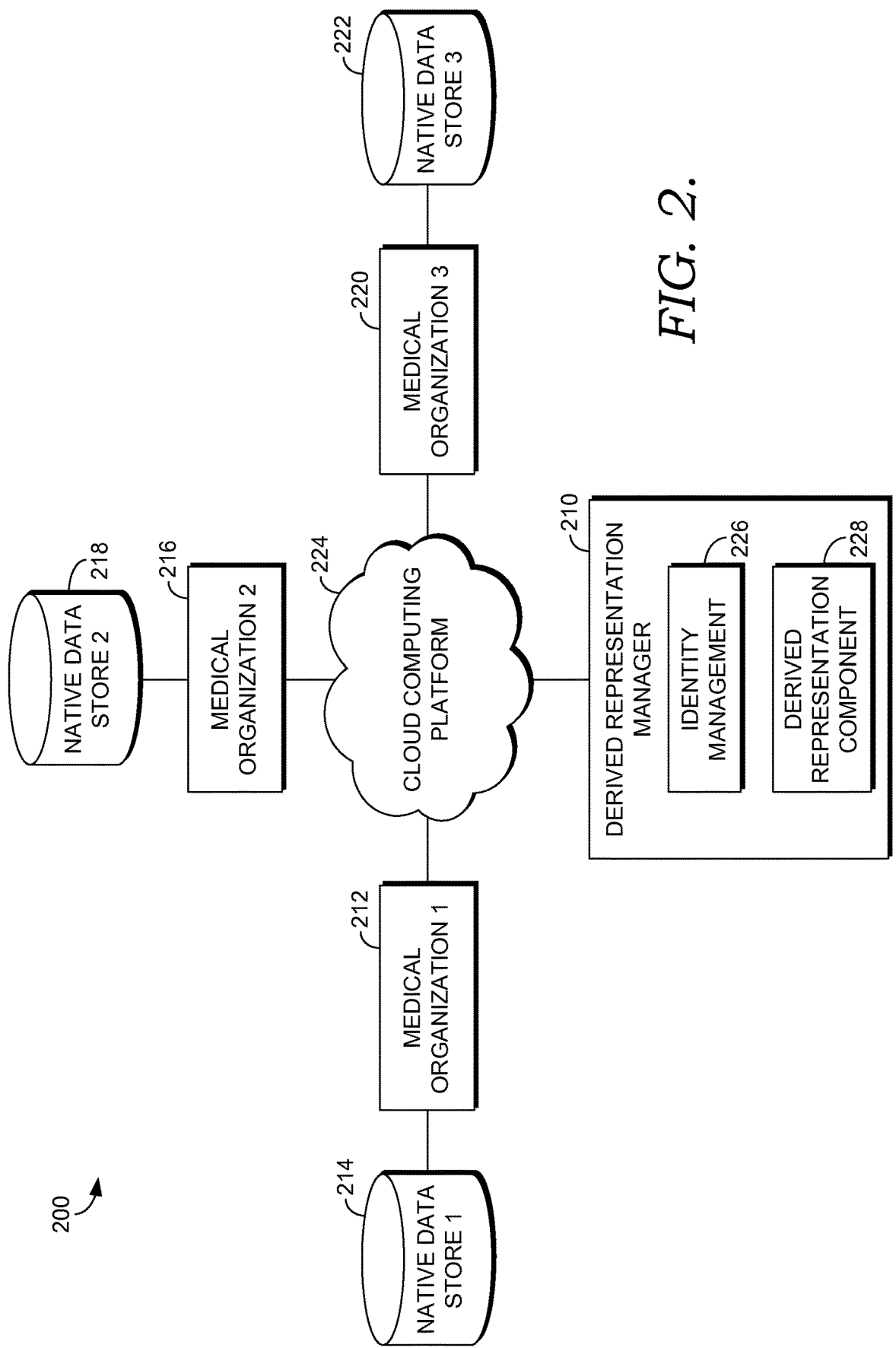
FIG. 2 is a block diagram showing an exemplary architecture for facilitating the aggregation and processing of healthcare information suitable to implement embodiments of the present invention.

Turning now to FIG. 2, a block diagram 200 is illustrated, in accordance with an embodiment of the present invention, showing an exemplary cloud computing platform 224 for use by a derived representation manager 210. It will be understood and appreciated that the cloud computing platform 224 shown in FIG. 2 is merely an example of one suitable computing system environment and is not intended to suggest any limitation as to the scope of use or functionality of embodiments of the present invention. For instance, the cloud computing platform 224 may be a public cloud, a private cloud, or a dedicated cloud. Neither should the cloud computing platform 224 be interpreted as having any dependency or requirement related to any single component or combination of components illustrated therein. Further, although the various blocks of FIG. 2 are shown with lines for the sake of clarity, in reality, delineating various components is not so clear, and metaphorically, the lines would more accurately be grey and fuzzy. In addition, any number of physical machines, virtual machines, data centers, endpoints, or combinations thereof may be employed to achieve the desired functionality within the scope of embodiments of the present invention. As mentioned, the cloud computing platform 224 comprises a cloud-computing network, which is known in the art as "the cloud."

The cloud computing platform 224 includes a data center configured to host and support the operation of the manager 210. The manager 210 refers to any software, or portions of software, that runs on top of, or accesses storage locations within, the platform 224. It will be appreciated that cloud computing platform 224 may include multiple computing devices such as computing devices or portions of computing devices 100 shown in FIG. 1. Cloud computing platform 224 may include virtual machines, such as software, application, operating system, or program that is executed by a processing unit to underlie the functionality of the derived representation manager 210. Further, the virtual machines may include processing capacity, storage locations, and other assets to support the derived representation manager 210.

In one aspect, the cloud computing platform 224 can communicate internally through connections dynamically made between the virtual machines and computing devices and externally through a physical network topology to resources of a remote network such as with medical organizations 212, 216, and 220. By way of example, the connections may include, without limitation, one or more local area networks (LANs) and/or wide area networks (WANs). Such networking environments are commonplace in offices, enterprise-wide computer networks, intranets, and the Internet. Accordingly, the network is not further described herein.

As shown in FIG. 2, the derived representation manager 210 is capable of communicating with a number of different entities or medical organizations such as the medical organizations 212, 216, and 220 for the collection of clinical information. As used throughout this application, the term "clinical information" is meant to be broad and encompass any type of healthcare information. The clinical information may be specific to a single patient or a group of patients. The clinical information may also be directed to a clinician or group of clinicians. For example, clinical information as it relates to a clinician may include patients that the clinician treats.

The organizations 212, 216, and 220 may include, for example, a hospital, a physician's office, a health information exchange, and an urgent care clinic. Clinical information collected from the different organizations 212, 216, and 220 may include, but is not limited to, information that describes various aspects of the patient state, including patient vitals, lab results, medication orders, diagnosis codes, condition codes, clinical orders, indexed values from clinical notes or other text documents, patient demographic information, patient history, patient images, and a variety of other patient information.

It should be noted that the medical organizations shown as communicating with the derived representation manager 210 in FIG. 2 are provided by way of example only and are not intended to limit the scope of the present invention in any way. Each medical organization 212, 216, and 220 may have one or more computing devices such as computing device 100 of FIG. 1, for communicating with the derived representation manager 210. Each medical organization 212, 216, and 220 maintains its own native electronic medical record system represented by a native data store (1) 214, a native data store (2) 218, and a native data store (3) 220 associated with the first, second, and third medical organizations respectively. Further, the medical organizations 212, 216, and 220 are not directly connected with one another such that the native data stores 214, 218, and 222 are utilized only by the data stores' respective medical organizations. The medical organizations 212, 216, and 220 send information to the cloud computing platform 224 and not typically directly between one another. In addition, communication between the manager 210 and the various medical organizations may be via one or more networks, which may comprise one or more wide area networks (WANs) and one or more local area networks (LANs), as well as one or more public networks, such as the Internet, and one or more private networks.

Further, the medical organizations 212, 216, and 220 may be able to access the manager 210 in a variety of ways within the scope of the present invention. For example, in some embodiments, a medical organization may have a native clinical computing system, which may be able to communicate with the manager 210. In other embodiments, a client application associated with the manager 210 may reside or partially reside on one or more of the medical organization's computing devices facilitating communication with the manager 210. In further embodiments, communication may simply be a web-based communication, using, for example, a web browser to communicate to the manager 210 via the Internet. Any and all such variations are contemplated to be within the scope of embodiments of the present invention.

The derived representation manager 210 is available in the cloud computing platform 224 in a manner that enables cross-venue recognition of a patient through the use of a patient identity management component 226 such as an Electronic Master Person Index (EMPI). Patient identity management component 226 enables the manager 210 to match data for the same patient that originates from different medical organizations or sources. Processing elements of a derived representation component 228 receive historical and new information for an individual patient that is sent to the cloud platform 224 and use this information to generate or update derived representations of the information. The derived representations of clinical information are immediately available to, for example, a clinician via a computer application regardless of the clinician's location.

Figure 3:
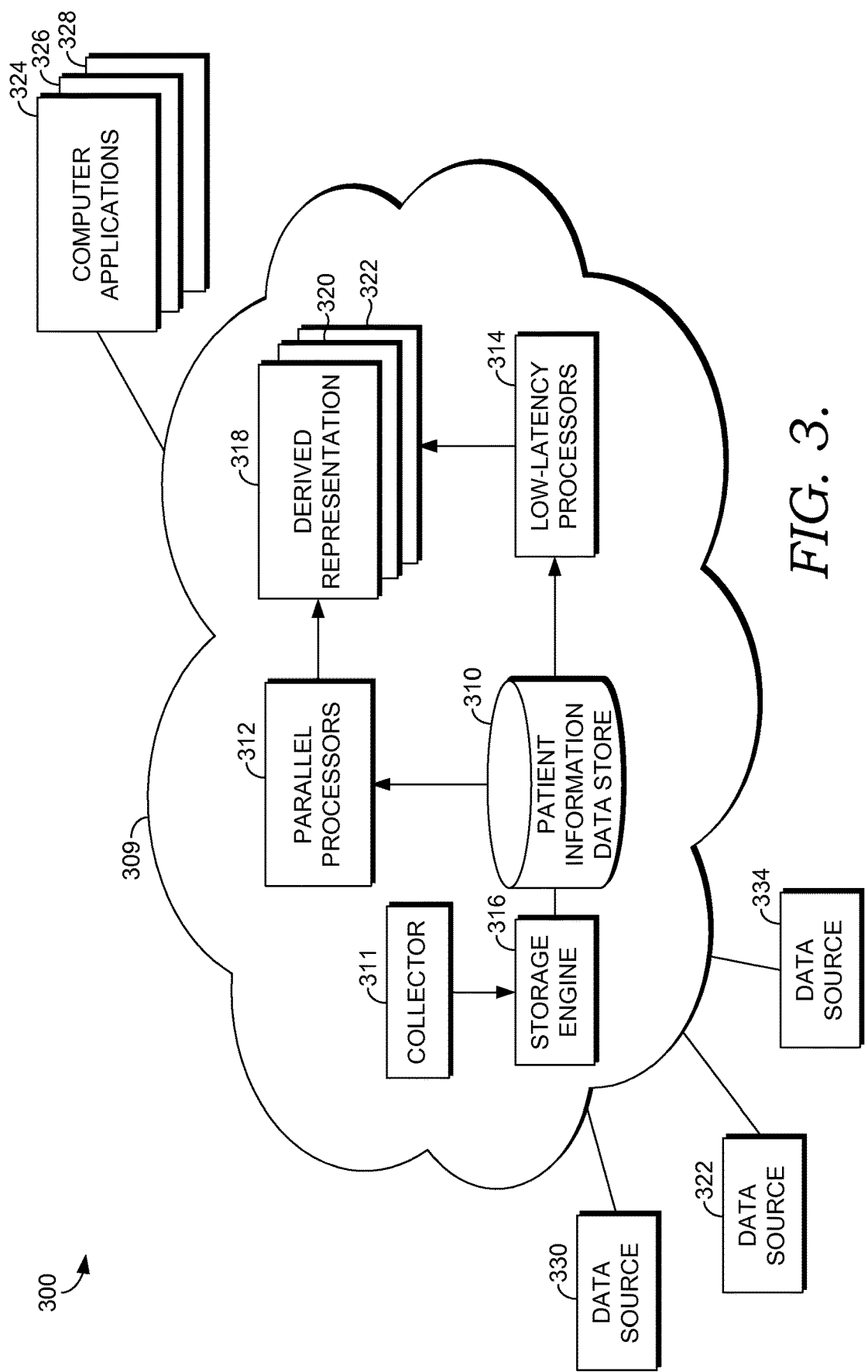
FIG. 3 is a block diagram of an exemplary system for creating derived representations using aggregated patient information suitable to implement embodiments of the present invention.

FIG. 3 depicts a more detailed view of the derived representation component 228 of FIG. 2 (now labeled as derived representation component 309 in system 300). The derived representation component 309 includes a collector 311, a storage engine 316, a patient information data store 310, one or more parallel processors 312, and one or more low-latency processors 314.

FIG. 3 includes data sources 330, 332, and 334. The data sources 330, 332, and 334 may include native data stores associated with one or more medical organizations such as the native data stores 214, 218, and 222 of FIG. 2. The data sources 330, 332, and 334 may also include data from one or more health information exchanges. The data sources 330, 332, and 334 store information including patient records, such as electronic medical records (EMRs) that can be accessed by various applications. For instance, a particular patient's EMR may be accessed by one or more providers associated with different medical organizations. Further, a patient's EMR may not be accessed by a particular provider at a particular medical organization but may be populated by patient information received from that provider at the medical organization.

The patient information stored in association with the data sources 330, 332, and 334 is received by the collector 311 by one of several methods. For instance, the collector 311 may include, in one aspect, a program that synchronizes data from the data sources 330, 332, and 334 to the collector 311 (hereinafter known as the "synchronization process"). The synchronization process extracts relevant information for a particular patient from the patient's EMR. The information may include a complete historical record of a patient's EMR. The information extracted by the synchronization process may also include any updates or modifications to the patient's EMR. Updates are received by the collector 311 substantially simultaneously with when the information is updated in the patient's EMR. In another aspect, the collector 311 may query the data sources 330, 332, and 334 to obtain patient information. Although the collector 311 is discussed in the context of a particular patient's EMR, it is contemplated that the collector 311 receives information concerning a multitude of patients.

The collected patient information may be received in any number of structures or formats. For example, information may be received from one data source in a relational format but be received by another data source in a hierarchical format. Further, the information received from both of these data sources may be directed to a single piece of data such as, for example, a blood glucose level. Thus, blood glucose levels may be received in multiple different formats depending upon the characteristics of the EMR system from which they were received. Additional structures or formats include HL7 feeds, Continuity of Care Documents (CCDs), and electronic data interchange (EDI) files containing medical claims information.

The derived representation component 309 further includes the storage engine 316 which stores the clinical information (historical and updated information) received by the collector 311. The storage engine 316 stores the collected information under a structured key in the patient information data store 310. In one aspect, the storage engine 316 may perform minimal restructuring on the clinical information prior to storing the information in the patient information data store 310. For example, if the clinical information is received in a relational model, the storage engine 316 may convert each row in the relational model into an independent document. The patient information data store 310 is sharded in order to support petabyte-scale data sets. For example, each shard may store up to 6-12 terabytes of clinical information.

In one aspect, the storage engine 316 stores related clinical information (e.g., information from a single patient) in a single storage shard to facilitate accessing and processing the information at substantially the same time. In another aspect, the storage engine 316 may spread related clinical information across multiple shards that are within close proximity of one another. Further, the storage engine 316 is configured to copy the clinical information to multiple shards to prevent loss of data if a physical machine fails.

The derived representation component 309 further includes the one or more parallel processors 312. The parallel processors 312 are configured for large-scale processing of historical clinical information in parallel to generate, for example, derived representations 318, 320, and 322 of the historical information using, for example, a map and reduce strategy. The parallel processors 312 are physically located next to the patient information data store 310. Even further, each parallel processor 312 generally accesses data or clinical information from a single shard of the patient information data store 310 to improve processing speeds.

Derived representations 318, 320, and 322 are representations of clinical data directed to specific use cases or clinical applications. Clinical use cases are myriad but may include semantic searching, timelines, population analytics, care management, alerts such as sepsis alerts, scheduling, patient summary lists, and the like. Each parallel processor 312 is a host for one or more codes, each code used to generate a derived representation 318, 320, or 322. If a new clinical need arises, code may be deployed to the parallel processor 312 to create a new derived representation that meets this need. Although only three derived representations are shown in FIG. 3, it is contemplated that each parallel processor 312 can generate a multitude of derived representations. By way of illustrative example, a clinical use case that exploits the power of the present system is care management in the context of population analytics. In this clinical use case, patient data may be aggregated across a large population (e.g., a population of a town or city) to identify patients in the population who are at risk for certain conditions such as diabetes. Community-wide prevention measures may then be implemented to manage patients at risk. This type and quantity of patient data is normally not aggregated and the computational power is typically not available to process these large sets of data.

As mentioned above, the parallel processors 312 act on historical clinical information. Thus, after the collector 311 performs an initial synchronization of the data sources 330, 332, and 334, a historical record of all the clinical information associated with a particular patient is stored in the patient information data store 310; the clinical information is drawn from disparate data sources and may be structured in a variety of formats. The parallel processors 312 act on this information to pre-create historical derived representations (such as derived representations 318, 320, and 322) of the patient's information. The pre-created derived representations 318, 320, and 322 are accessible to a variety of computer applications 324, 326, and 328. Further, the derived representations 318, 320, and 322 are updated as new information becomes available; this process will be explained in greater depth below.

A parallel processor 312 generates a historical derived representation by first identifying a subset of the patient information stored in the data store 310 that is needed to generate a particular derived representation (which, in turn, is directed to a particular clinical need). The subset of patient information may be in different formats due to the disparate nature of the EMR systems from which the information was received or the disparate ways in which information is stored in a single EMR. By way of example, if the clinical need is a trending display of a lab result, then the subset of patient information would include all values of the lab result stored in the patient information data store 310.

The parallel processor 312 then restructures the subset of patient information to generate a derived representation (e.g., derived representation 318) of the subset of patient information; the derived representation may be structured differently from the subset of patient information. The derived representation is available to a computer application (e.g., computer application 324) that presents this data to clinicians associated with the patient's care, regardless of where the clinician is located. The same subset of patient information may be used to generate a second derived representation (e.g., derived representation 326) directed to a different clinical need (e.g., a patient summary chart). The second derived representation may be structured differently than the derived representation directed toward the trending display. Thus, a subset of patient information, though received in a variety of different formats, may be used to generate multiple derived representations, each formatted differently and each directed to a clinical need.

The derived representation component 309 further includes the one or more low-latency processors 314 configured to update in real time the derived representations 318, 320, and 322 when new information becomes available. Each low-latency processor 314 is generally associated with a particular derived representation and subscribes to updates directed to a subset of patient information associated with the particular derived representation. For example, if a derived representation is directed to a trending display of a patient's blood glucose levels, the low-latency processor 314 would subscribe to updates to the patient's blood glucose levels regardless of the source of the update.

Updates are streamed in real time to the low-latency processor 314 via the synchronization process as the updates occur. For instance, a data item, such as a medication order, may be updated in a data source, such as the data source 330, and pushed to the collector 311 via the synchronization process; the data item is received from the data source in a first format. The collector 311 then notifies the low-latency processor 314 that an update or change has occurred and the updated data item is available for processing. The collector 311 pushes the updated data item to the low-latency processor 314. The low-latency processor 314 determines that its associated derived representation includes an outdated version of the data item; the derived representation is in a second format. The low-latency processor 314 updates its associated derived representation by restructuring the data item from the first format to the second format and replacing the outdated version of the data item in the derived representation with the reformatted updated data item. The updated derived representation is immediately available to one or more computer applications. The result is that updates to a patient's EMR are immediately available to clinicians, thus enhancing patient care.

As mentioned, the low-latency processor 314 subscribes to a specific subset of patient information associated with a specific derived representation. The subset of patient information may be received from multiple data sources and may be structured differently depending on characteristics of the originating data source. Even though the subset of information may be in multiple different formats, the low-latency processor 314 is configured to restructure the different formats into a uniform format compatible with the derived representation.

The low-latency processor 314 is further configured to access patient information stored in the patient information data store 310 prior to processing the subset of patient information in order to provide context for the subset of patient information. For instance, the subset of patient information may comprise a lab result for a blood glucose level for a particular patient. The low-latency processor 314 may access additional clinical information associated with the patient to determine the context of the blood glucose level—was it a fasting blood glucose level or was it taken immediately after a meal? Based on the additional clinical information, the low-latency processor 314 may ignore the blood glucose level, discard the blood glucose level, or process the data and update the derived representation associated with the low-latency processor 314.

Turning now to FIG. 4, a flow diagram is depicted of an exemplary method 400 of utilizing clinical information in disparate formats to generate one or more derived representations of the clinical information. The method may be carried out by one or more parallel processors such as the parallel processor 312 of FIG. 3. As mentioned above, each of the parallel processors may be associated with a storage shard and processes related clinical information (e.g., information associated with a single patient) stored in the storage shard.

At a step 410, a first set of patient information for a patient is received by, for example, the parallel processor; the first set of patient information is structured in a first format. The first set of patient information may comprise part or all of a patient's EMR and may be received from a first medical organization. The medical organization may include a hospital, a clinician's office, a minute clinic, an urgent care clinic, and/or a health information exchange.

At a step 412, a second set of patient information for the patient is received by, for example, the parallel processor. The second set of patient information may be structured in a second format. The second set of patient information may comprise part or all of a patient's EMR and may be received from a second medical organization. Further, the first and second medical organizations may structure information in their electronic medical record systems differently (e.g., hierarchical versus relational).

Alternatively, the first and second set of patient information may be received from a single medical organization. Even though both sets of information are received from a single medical organization, the first set of patient information may still be structured differently from the second set of patient information. This may occur, for example, when different parts of the patient's medical record are stored on different tables, and the tables are structured differently. Patient data within a single medical organization that is structured differently and is stored in disparate locations within the EMR has historically been difficult to query, and generating a clinically-relevant view of this data has historically taken a long time.

The first and second set of patient information may be directed toward the same data item. This occurs for example when a patient has a lab result (e.g., a lab result for a blood glucose level) at both the first and second medical organization, or a lab result at a single medical organization is associated with two different data models or tables. Conversely, the first and second set of patient information may be directed toward different data items.

At a step 414, the first and second sets of patient information are restructured by the parallel processor to generate a first derived representation of the patient information; the first derived representation may be in a third format that is different from both the first and second format. The first derived representation is configured for use by a first computer application directed to a particular clinical need such as scheduling, patient summary, trending information, and the like.

At a step 416, the first and second sets of patient information are restructured by the parallel processor to generate a second derived representation of the patient information. The second derived representation may be in a fourth format that is different from the first, second, and third formats. The second derived representation is configured for use by a second computer application directed to a clinical need. As can be seen, a set(s) of patient information may be restructured in any number of ways to create any number of derived representations adapted for any number of clinical needs.

Further, requests from computer applications for the first and second derived representations may be received. For example, the first computer application may request the first derived representation, and the second computer application may request the second derived representation. The first derived representation may subsequently be communicated to the first computer application, and the second derived representation may be communicated to the second computer application. Both the first and second computer applications may be used by a clinician who desires access to patient information. The clinician may access the computer applications and view information associated with a patient that is drawn from multiple medical facilities without being present at any of those medical facilities.

Turning now to FIG. 5, FIG. 5 depicts a flow diagram of an exemplary method 500 of updating a pre-created derived representation of patient information; the pre-created derived representation may have been generated by a parallel processor using historical clinical information. The method 500 may be carried out by one or more low-latency processors such as the low-latency processors 314 of FIG. 3. Each low-latency processor may be associated with a derived representation directed to a specific clinical need.

At a step 510, a first set of patient information for a patient is received from a first medical organization substantially simultaneously with the first medical organization updating the information in the patient's EMR. The first set of patient information may be structured in a first format. Each low-latency processor subscribes to patient information utilized by the low-latency processor's associated derived representation. Thus, any time the subscribed information is updated in, for example, an EMR of an organization, the updated information is streamed in real time to the low-latency processor.

At a step 512, it is determined that the derived representation includes an outdated version of the first set of patient information; the derived representation is in a second format. At a step 514, the first set of patient information is restructured from the first format to the second format. At a step 516, the derived representation is updated by replacing the outdated version of the first set of patient information with the first set of patient information in the second format. The result is a first updated derived representation. The first updated derived representation may be communicated to a computer application utilizing the historical derived representation.

The method 500 may be continued further. For example, a second set of information for the patient may be received from a second medical organization substantially simultaneously with the second medical organization updating the information in the patient's EMR. The EMR systems of the first and second medical organizations may structure data differently. Thus, the second set of patient information may be in a third format that is different from the first and second formats.

It may be determined that the first updated derived representation includes an outdated version of the second set of patient information. The second set of patient information may be restructured from the third format to the second format (the first updated derived representation being in the second format). The first updated derived representation may be updated yet again using the restructured second set of patient information. Thus, a derived representation may be updated every time information associated with the derived representation is updated or modified. The second updated derived representation is immediately made available to the computer application.

A real-life example will be provided to better illustrate the claimed invention. Clinicians often desire to look at a patient's data during a certain time range—a so-called timeline view. The data may include, for example, lab values associated with the disease Diabetes Mellitus Type I. The lab values may include fasting blood glucose levels, and glycosylated hemoglobin levels. Previously, the timeline view could only be generated using data from an EMR associated with a single facility. Even then, the lab values were distributed among different data models within the facility's EMR system. In order to generate the timeline, different queries directed to the different data models were generated to retrieve the needed information—this method has a high computational cost and introduces lag between when a value is updated in the patient's EMR and when it is accessible to a clinician. Aspects of the present invention combine these different data elements present within a single EMR system, although structured differently, and pre-computes the timeline view so that it is instantly available when the clinician needs to access the timeline view.

The present invention aggregates the lab values from one or multiple medical organizations and stores the data; the data may be structured in a variety of formats. For instance, a fasting blood glucose level and a glycosylated hemoglobin level for the patient may be received from an urgent care clinic that the patient visited in the past. Additional fasting blood glucose levels and glycosylated hemoglobin levels may be received from the patient's primary care provider's office. Each set of data may be structured in different formats. The received data is associated with the patient using, for example, an electronic master patient index and stored in a storage shard.

Continuing, a parallel processor is configured to generate a derived representation in the form of a timeline of lab values. The fasting blood glucose levels and glycosylated hemoglobin levels from both the urgent care clinic and the provider's office are received by the parallel processor and restructured to generate a derived representation of the lab values. The derived representation is immediately available to a computer application that presents the timeline on a user interface. Any updates to the lab values from the urgent care clinic or the provider's office are received in real time and used to update the derived representation. Further, if the patient visits, for example, an emergency room and has a fasting blood glucose level and a glycosylated hemoglobin level drawn, this information may also be used to update the derived representation in real time. The updated derived representations are immediately available to the computer application. Thus, a clinician involved in the patient's care has up-to-date access to patient information, even if the information is drawn from multiple sources.

Figure 6:
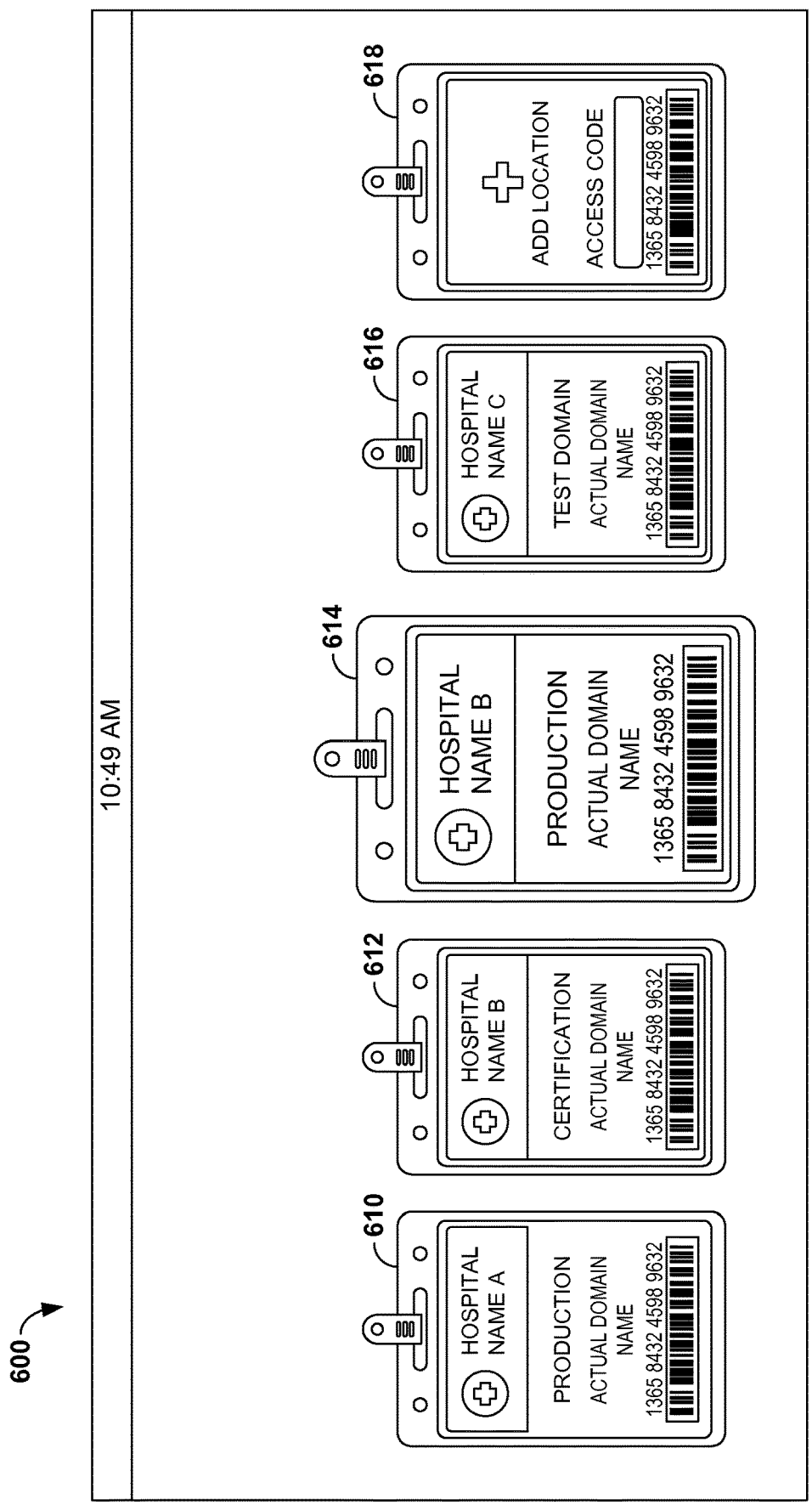
FIG. 6 depicts an exemplary graphical user interface illustrating a log-in screen to a computer application that presents clinical information from disparate electronic medical record systems in accordance with an embodiment of the present invention.

Turning to FIG. 6, an exemplary graphical user interface (GUI) 600 is depicted. The GUI 600 is a log-in screen of an application that presents patient information from multiple disparate data sources. The GUI 600 may be presented to one or more clinicians upon accessing the application. As can be seen, the GUI 600 includes a number of different selectable options 610, 612, 614, 616, and 618. A clinician may be able to access information associated with one or more of the different selectable options 610, 612, 614, 616, and 618 after undergoing an authentication and authorization protocol. For example, a first clinician may have hospital privileges with Hospital Name B (options 612 and 614) but not with Hospital Name A (option 610) or with Hospital Name C (option 616). The first clinician is able to access his patient's information through the options 612 and 614 after undergoing authentication and authorization. Conversely, a second clinician may have hospital privileges with Hospital Name C and may be able to access her patient's information by selecting option 616. The GUI 600 further includes the option 618 which enables a clinician to add a facility by entering an access code provided by, for example, the facility.

Figure 7:
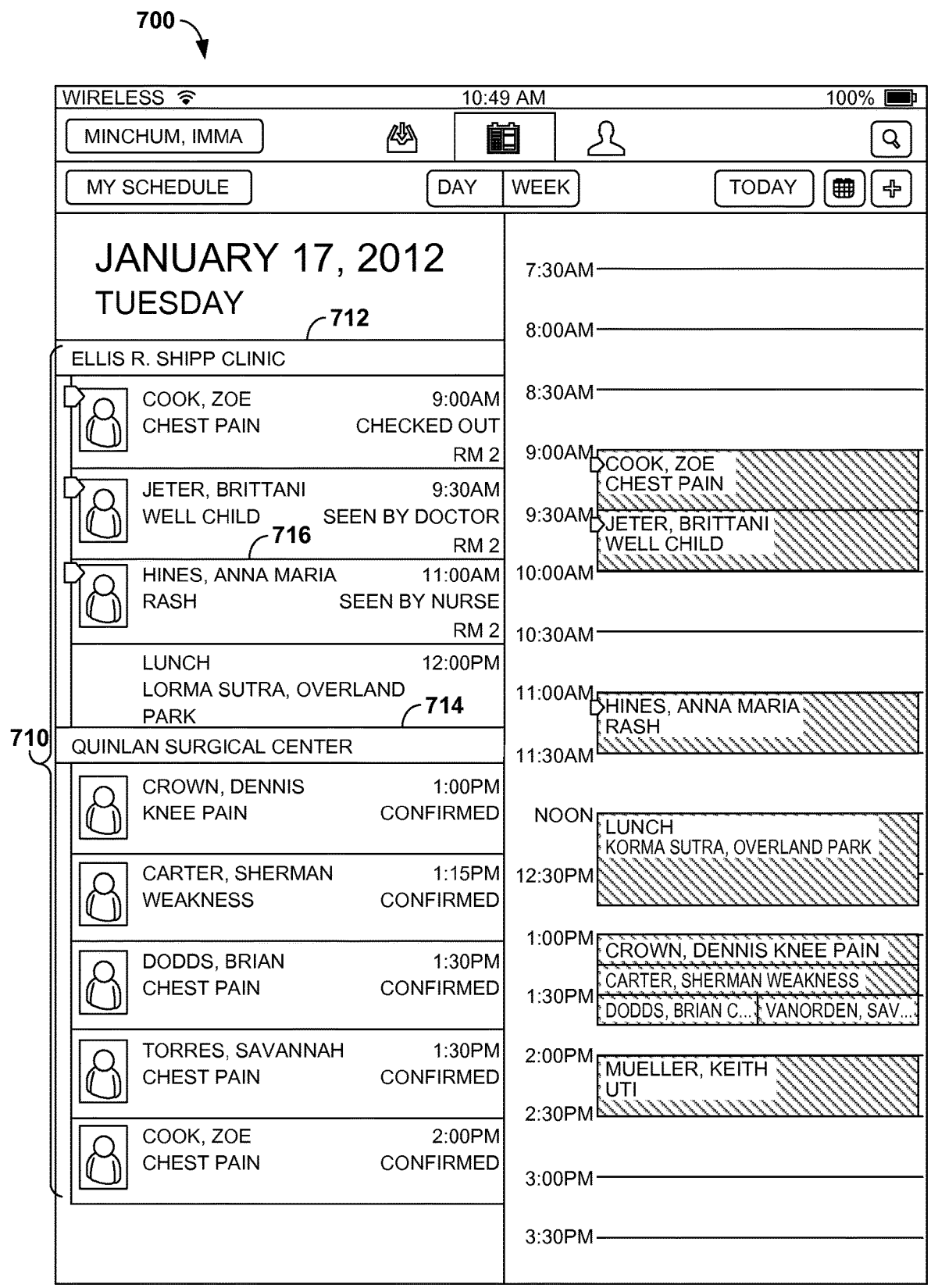
FIG. 7 depicts an exemplary graphical user interface for presenting on a single user interface clinical information from disparate electronic medical record systems in accordance with an embodiment of the present invention.

FIG. 7 depicts an exemplary graphical user interface (GUI) 700 that may be presented to a clinician after the clinician has undergone authentication and authorization. The GUI 700 depicts a schedule 710 associated with the clinician. The schedule 710 is generated using patient information drawn from two different facilities—the Ellis R. Shipp Clinic 712 and the Quinlan Surgical Center 714. The schedule 710 may be generated from a derived representation created by a derived representation component such as the derived representation component 228 of FIG. 2. As shown, the schedule 710 represents a comprehensive listing of all the clinician's patients, even though the patients are associated with different medical facilities. Each of the patients on the schedule 710 is selectable. Although not shown, the schedule 710 is updated in real time as patients are added or cancelled from the list. The updated schedule 710 is generated from an updated derived representation created by a derived representation component such as the derived representation component 228 of FIG. 2.

FIG. 8 depicts an exemplary graphical user interface (GUI) 800 that is presented to the clinician upon selection of a patient, such as selection of the patient 716 on GUI 700. The GUI 800 is directed to clinical orders and includes three sections: medications 810, labs 812, and imaging 814. The information presented in these three sections 810, 812, and 814 may have been drawn from multiple disparate data sources and be structured in multiple, different formats. The information is restructured by a derived representation component such as the derived representation component 228 of FIG. 2 to create a derived representation directed to clinical orders. Information presented on the GUI 800 may be updated in real time as updated information becomes available. For instance, a clinical order may have been entered for the patient in a facility's EMR system; the clinical order discontinues the medication Augmentin. This updated information would be instantly available on the GUI 800.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer storage media, executable by a computing system having a plurality of parallel processors and a plurality of low-latency processors operating on a cloud computing platform, for facilitating a method of utilizing patient data in disparate formats to generate derived representations of the patient data, the method comprising:

receiving, via a computing device, a first set of patient data directed to a particular data item for a patient from a first medical organization, the first set of patient data structured in a first format;

receiving, via a computing device, a second set of patient data directed to the particular data item for the patient from a second medical organization, the second set of patient data structured in a second format that is different from the first format, the first medical organization and the second medical organization being disparate such that they do not share patient data with each other, wherein at least the first format is incompatible with a first computer application, and wherein at least the second format is incompatible with a second computer application;

generating, using at least one of a plurality of parallel processors, a first derived representation of the particular data item, the first derived representation generated using the first and second sets of patient data, the first derived representation structured in a third format, wherein the third format is configured for use by the first computer application directed to a first clinical need, wherein the first computer application comprises a population analytic process; and generating a second derived representation of the particular data item comprising an alert related to the particular data item, the second derived representation generated using the first and second sets of patient data, the second derived representation structured in a fourth format, wherein the fourth format is configured for use by the second computer application directed to a second clinical need;

receiving a request from the first computer application or the second computer application for the first derived representation or the second derived representation respectively; and communicating for presentation on a user interface associated with the first computer application or the second computer application the first derived representation or the second derived representation respectively.

2. The media of claim 1, wherein the first medical organization and the second medical organization maintain disparate medical record systems.

3. The media of claim 2, wherein the first computer application and the second computer application are both useable by a clinician associated with at least one of the first medical organization or the second medical organization.

4. One or more non-transitory computer storage media, executable by a computing system having a plurality of parallel processors and a plurality of low-latency processors operating on a cloud computing platform, for facilitating a method of updating derived representations of patient data, the method comprising:

receiving, via a computing device, a first set of patient data structured in a first format from a first medical organization substantially simultaneously with the first medical organization updating the first set of patient data in an electronic medical record system associated with the first medical organization, the first set of patient data directed to a particular data item, the first format comprising a relational model, the relational model comprising a plurality of rows of data;

receiving, via a computing device, a second set of patient data structured in a second format from a second medical organization substantially simultaneously with the second medical organization updating the second set of patient data in an electronic medical record system associated with the second medical organization, the first medical organization and the second medical organization being disparate such that they do not share patient data with each other, the second set of patient data directed to the particular data item;

determining that a derived representation comprising a timeline view of the particular data item includes an outdated version of the first set of patient data and includes an outdated version of the second set of patient data, wherein the derived representation is structured in a third format;

reformatting, using at least one of a plurality of low-latency processors the first and second sets of patient data into the third format, wherein reformatting the first set of patient data comprises converting the relational model such that an independent document is generated for each of the plurality of rows of data;

generating a new derived representation comprising a new timeline view of the particular data by item by replacing the outdated version of the first and second sets of patient data with the reformatted set of patient data;

receiving a request from a computer application for the new derived representation; and communicating for presentation on a user interface associated with the computer application the new derived representation.

5. The media of claim 4, further comprising:
wherein the computer application is directed to a particular clinical need.

6. The media of claim 4, wherein the computer application is utilized by a clinician associated with at least one of the first medical organization or the second medical organization.

7. A cloud computing platform for processing and updating derived representations of patient data using a plurality of parallel processors and at least one low-latency processor, the cloud computing platform comprising:

a storage engine, located at a central location, wherein the storage engine:
receives sets of patient data directed to a particular data item for a patient from a plurality of disparate medical organizations, the sets of patient data received in a plurality of different formats, wherein the plurality of disparate medical organizations do not share patient data with each other; and receives updates to the sets of patient data directed to the particular data item from at least a portion of the plurality of medical organizations, the updated sets of patient data received substantially simultaneously with the at least the portion of the plurality of medical organizations updating the sets of patient data in electronic medical record systems associated with each of the medical organizations, the updated sets of patient data received in a plurality of different formats;

a plurality of parallel processors that:
receive the sets of patient data from the storage engine;
generate a first derived representation of the sets of patient data using at least one code, wherein each parallel processor of the plurality of parallel processors is a host for the at least one code, the first derived representation comprising a first alert related to the particular data item, the first derived representation structured in a uniform first format, wherein the at least one low-latency processor:
receives the updated sets of patient data from the storage engine;
reformats the updated sets of patient data from the plurality of different formats into the uniform first format; and
generates a first updated derived representation comprising a second alert by updating the first derived representation with the reformatted updated sets of patient data; and a communication component that:
receives requests from a computer application for the first derived representation or the first updated derived representation; and
communicates the first derived representation or the first updated derived representation for presentation on a user interface associated with the computer application.

8. The system of claim 7, wherein the storage engine is further operable to store the sets of patient data and the updated sets of patient data in a first set of storage shards.

9. The system of claim 8, wherein the storage engine is further operable to:
copy the sets of patient data and the updated sets of patient data; and
store the copies in a second set of storage shards.

10. The system of claim 7, wherein the updated sets of patient data are received by the storage engine at a point in time after the sets of patient data are received by the storage engine.

11. The system of claim 7, wherein the at least one low-latency processor:
queries the storage engine for an additional set of patient data for the patient; and
uses the additional set of patient data for the patient to determine that the first derived representation should be updated.

* * * * *